(12) United States Patent  
Klein

(10) Patent No.: US 9,282,950 B2
(45) Date of Patent: *Mar. 15, 2016

(54) CERVICAL CELL TISSUE SELF-SAMPLING DEVICE

(71) Applicant: GyneConcepts, Inc., Atlanta, GA (US)

(72) Inventor: Philip Klein, Atlanta, GA (US)

(73) Assignee: GYNECONCEPTS, INC., Atlanta, GA (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/192,989

(22) Filed: Feb. 28, 2014

(65) Prior Publication Data

US 2014/0249450 A1    Sep. 4, 2014

Related U.S. Application Data

(63) Continuation of application No. 13/900,173, filed on May 22, 2013, now Pat. No. 8,672,861, which is a continuation of application No. 13/600,869, filed on Aug. 31, 2012, now Pat. No. 8,460,209.

(60) Provisional application No. 61/532,724, filed on Sep. 9, 2011.

(51) Int. Cl.
*A61B 5/00* (2006.01)
*A61B 10/02* (2006.01)

(52) U.S. Cl.
CPC ..... *A61B 10/0291* (2013.01); *A61B 2010/0216* (2013.01)

(58) Field of Classification Search
CPC ............... A61B 10/02; A61B 10/0291; A61B 2010/0216; A61B 2010/0225; A61B 2010/0233

See application file for complete search history.

(56) References Cited

U.S. PATENT DOCUMENTS

| | | |
|---|---|---|
| 3,995,618 A | 12/1976 | Kingsley et al. |
| 4,157,709 A | 6/1979 | Schuster et al. |
| 4,628,941 A | 12/1986 | Kosasky |
| 4,662,381 A | 5/1987 | Inaba |
| 4,735,905 A | 4/1988 | Parker |
| 5,129,402 A | 7/1992 | Koll et al. |
| 5,191,899 A | 3/1993 | Strickland et al. |
| 5,348,023 A | 9/1994 | McLucas |
| 5,445,164 A | 8/1995 | Worthen et al. |
| 5,787,891 A | 8/1998 | Sak |
| 5,795,309 A | 8/1998 | Leet et al. |
| 5,874,045 A | 2/1999 | Chisum |
| 5,971,996 A | 10/1999 | Tugendreich et al. |

(Continued)

OTHER PUBLICATIONS

PCT International Search Report for PCT Application No. PCT/US2012/053355 mailed Dec. 20, 2012.

(Continued)

*Primary Examiner* — Max Hindenburg
(74) *Attorney, Agent, or Firm* — Sutherland, Asbill & Brennan LLP

(57) ABSTRACT

A device, a kit, and a method of use thereof, for self-administration and collection of cervical cell tissue samples such as for Pap smear testing. The device comprises an insertion tube, within which is carried a movable cervical aligning tool with an aligning probe, and a cellular sampling tool with a cellular adhesion surface. The aligning probe and cellular adhesion surface can be selectively movable relative to the insertion tube to improve accuracy of the testing and user safety.

20 Claims, 11 Drawing Sheets

(56) References Cited

U.S. PATENT DOCUMENTS

| | | |
|---|---|---|
| 6,083,177 A | 7/2000 | Kobren et al. |
| 6,155,990 A | 12/2000 | Fournier |
| 6,171,259 B1 | 1/2001 | Fisher |
| 6,197,327 B1 | 3/2001 | Harrison et al. |
| 6,302,853 B1 | 10/2001 | Sak |
| 6,364,832 B1 | 4/2002 | Propp |
| 6,387,058 B1 | 5/2002 | Wallach |
| 6,394,966 B1 | 5/2002 | Gill et al. |
| 6,475,165 B1 | 11/2002 | Fournier |
| 6,669,643 B1 | 12/2003 | Dubinsky |
| 6,740,049 B2 | 5/2004 | Wallach |
| 6,926,677 B2 | 8/2005 | Richards |
| 7,087,028 B2 | 8/2006 | Sak |
| 7,165,550 B1 | 1/2007 | Tracy et al. |
| 7,648,681 B2 | 1/2010 | Meyer et al. |
| 2002/0026157 A1 | 2/2002 | Fournier |
| 2002/0111562 A1 | 8/2002 | Richards |
| 2004/0153000 A1 | 8/2004 | Pevoto |
| 2005/0215920 A1 | 9/2005 | Isa |
| 2005/0256440 A1 | 11/2005 | Zunker et al. |
| 2005/0277846 A1 | 12/2005 | Chou |
| 2005/0277847 A1 | 12/2005 | Belinson |
| 2008/0188769 A1 | 8/2008 | Lu |
| 2009/0062690 A1 | 3/2009 | Kim |
| 2009/0275859 A1 | 11/2009 | Kim |
| 2011/0087133 A1 | 4/2011 | Ching et al. |

OTHER PUBLICATIONS

Supplementary European Search Report for EP Application No. 12830698.2 mailed Apr. 8, 2015 (6 pages).

CERVICAL CELL TISSUE SELF-SAMPLING DEVICE

CROSS-REFERENCE TO RELATED APPLICATIONS

This application is a continuation of U.S. patent application Ser. No. 13/900,173, filed May 22, 2013, allowed, which is a continuation of U.S. patent application Ser. No. 13/600,869, now U.S. Pat. No. 8,460,209 issued on Jun. 11, 2013, which application claims priority to U.S. Provisional Application Ser. No. 61/532,724, filed Sep. 9, 2011, the entire contents of which are incorporated by reference herewith.

FIELD OF INVENTION

The present invention relates to gynecological medical apparati and methods of use. More particularly, the present invention provides a device for self-collecting cervical tissue samples for Pap test screening for cervical cancer and other infectious diseases.

BACKGROUND OF THE INVENTION

The Pap test (a/k/a Pap smear, cervical smear, or Papanicolaou smear) is an important routine gynecological test usually performed annually to screen for early detection of cervical, uterine, and/or vaginal cancer. The Pap test is not intended to be a definitive diagnostic test, but rather a risk assessment-oriented, basic screening procedure. The Pap test is an anatomic pathology assay, where human tissue, cells, and/or secretions from the site of a potential cancer, such as the cervical region, are viewed under a microscope by a trained laboratory professional in search of cellular morphologic changes that evidence, to varying degrees along a standardized continuum of severity (e.g., the Bethesda System), the likely existence and progression of cervical cancer.

A positive Pap test where suspicious cellular changes have been identified is generally followed-up with a colposcopy and/or definitive biopsy. Importantly, given the inherently and otherwise unavoidably imprecise nature of the Pap test, the Pap test owes its legendary efficacy in preventing cervical cancer as much, if not more, to the sheer repetitiveness of the procedure over the course of a woman's life, than to the sensitivity, per se, of any single Pap test. According to cytology experts, the statistical confidence level of an accurate Pap test result rises from a low of 60-70% to upwards of 98% after just three consecutive annual Pap tests.

For this reason, health care standards-setting organizations, such as the American Cancer Society, generally recommend regular (e.g., annual) Pap testing for all women, and for sexually active teens. The American Cancer society recommends that normal women under forty have a Pap smear taken every three years after three consecutive yearly normal Pap smears. However, according to a Gallup poll conducted by the College of American Pathologists (CAP), nearly 40% of those women polled had not had a Pap test within the past year. For many women, the routine screening test would be regularly performed if it could be done in a non-intrusive, private manner. Screening for Cervical Cancer, in Common Screening Tests, David M. Eddy, MD, PhD, Editor, Chapter 10, pages 255-283 (1991).

The Pap test is traditionally taken by a gynecologist by inserting a speculum into the patient's vagina in a manner to expose the cervix of the uterus for sampling tissue, in particular for sampling cells from the endocervical canal and cervical os. To accomplish this, the woman must remain in a reclining position. Various types of speculums and numerous cervical scrapers or probes have been developed for this purpose. The cytologic specimens collected are then placed upon microscope slides for manual or automated reviewing. They are evaluated for hormonal levels and to determine the presence of cancers, precancers and vaginal infections. The test aims to detect potentially pre-cancerous changes (called cervical intraepithelial neoplasia (CIN) or cervical dysplasia), which are very often caused by sexually transmitted human papillomaviruses. The test remains an effective, widely used method for early detection of pre-cancer and cervical cancer. The test may also detect infections and abnormalities in the endocervix and endometrium.

Most of the prior art equipment has been designed for use by gynecologists and is not suitable for use solely by the patient upon herself. There have been previous attempts to develop Pap test apparatus that could be self-administered in order to achieve an economic efficiency by avoiding physician assistance, and improved healthcare through widespread availability. However, there remains a need to provide a more accurate, non-traumatic, self-administered apparatus and method for the collection of cervical tissue samples for cytologic evaluation.

SUMMARY OF THE INVENTION

This present invention provides a cervical cell tissue self-sampling device, and method of use thereof, that can be used at home or any location of a patient's choosing. The inventive device and method of self-administration and collection of vaginal cervical cell tissue samples provide an efficient tool for privately performing a Pap smear or tissue sample collection without the need for assistance by a gynecologist or other medical practitioner.

In certain embodiments, the present invention provides a device for collecting a cervical cell tissue sample comprising an elongated insertion tube shaped for insertion into the vagina of the patient and having a proximal end, a distal end, an exterior surface and an interior surface extending therethrough defining a passage.

The device further comprises an elongated cervical aligning tool shaped for insertion within the passage of the insertion tube, and having a proximal end with a handle (also referred to as an aligning tool handle, or "U-Ring") thereon, a distal end with a cervical aligning tool (also referred to as an aligning spoon) thereon, and a body therebetween, wherein the handle is disposed outside the proximal passage of the insertion tube for manipulation by the user. The aligning tool is movable between a first position for insertion, wherein the distal cervical aligning probe is contained within the passage of the insertion tube, and a second position for cervical cap alignment, wherein the cervical aligning probe advances to extend distally from the passage of the insertion tube to engage the posterior cervical fornix of the patient, in order to expose the os for cell specimen collection.

The device further comprises an elongated cellular sampling tool shaped for insertion within the passage of the insertion tube and upon a portion of the body of the elongated aligning tool within the advanceable U-Ring handle. The cellular sampling tool has a proximal end with an advancing ball-shaped handle thereon, and a distal end with a cellular adhesion surface, such as a small brush, thereon. The advancing handle of the sampling tool extends from the proximal passage of the insertion tube proximal to the U-Ring of the aligning tool for manipulation by the user. The cellular sampling tool is dependently, or releasably, movable between a first position for insertion wherein the distal cellular adhesion surface is contained within the passage of the insertion tube, and a second position for cervical cell tissue sampling wherein the distal cellular adhesion surface extends distally outside the passage of the insertion tube.

The movement of the cervical aligning tool and/or the cellular sampling tool is dependent upon the user selective release of a retaining mechanism by the direct or indirect action of the patient or other person using the device. In certain embodiments, the distal movement of the cervical aligning tool and/or the cellular sampling tool is dependent upon the patient removing, or releasing, a handle retaining safety cover which frictionally engages the insertion tube and the sampling tool and/or the cervical aligning tool in a fixed relative position until the retaining cover is removed. In certain other embodiments, the distal movement of the cellular sampling tool is dependent upon the patient manually disengaging a release tab on the cellular sampling tool in selective communication with the insertion tube. In other embodiments, the distal movement of the cellular sampling tool is dependent upon the patient moving the aligning tool into the second position, which indirectly releases a retaining pin on the sampling tool from a fixed position. These and other configurations for requiring the cellular sampling tool and/or the cervical aligning tool to be dependently or selectively releasably movable will be apparent to one of skill in the art in view of the present disclosure. The dependency of requiring the release of a retaining mechanism to allow distal movement of the cervical aligning tool and/or the cellular sampling tool protects the patient's tissue during insertion of the device and prevents premature exposure of the cellular adhesion surface within the vaginal wall to avoid non-specific contamination of the cervical cells of interest.

Following release of a retaining mechanism, the cellular sampling tool can be fully or partially movable distally and rotatable within the insertion tube and upon the spoon-shaped cervical aligning tool and U-Ring for gathering cervical cellular samples from and adjacent to the cervical os. In certain embodiments, the cellular adhesion surface is a brush element. In certain embodiments, the distal end of the brush element has a cone-shaped distal end with a high density of flexible bristles. In other embodiments, the cellular adhesion surface is separable from the cellular sampling tool and the rest of the device for storage and transportation of the cervical cell samples to a laboratory for analysis. In certain embodiments, the cellular sampling tool further comprises a retaining sleeve slideably disposed upon the sampling tool between a first position for retaining the adhesion surface and a second position for releasing the adhesion surface. In certain embodiments, the cellular sampling tool allows release of the adhesion surface by unscrewing the threaded distal end.

In certain embodiments, the cervical aligning probe is spoon-shaped having a convex curvature concentric with the distal end of the insertion tube. In other embodiments, the cervical aligning tool further comprises an aligning extension element, or keel, extending along a portion of the body which engages an elongated alignment groove extending from a portion of the interior surface of the insertion tube.

In certain embodiments, the U-Ring of the cervical aligning tool engages the proximal portion of the passage of the insertion tube to impede further distal movement of the cervical aligning tool within the vagina. In certain embodiments, the advancing handle of the cellular sampling tool engages the proximal portion of the U-Ring of the cervical aligning tool to impede further distal movement of the cellular sampling tool within the vagina.

In certain embodiments, the proximal end of the insertion tube further comprises an annular insertion shield peripherally extending from the exterior surface to impede insertion within the vagina beyond a predetermined depth. In certain embodiments, the annular insertion shield extends wider along a surface corresponding to the anterior of the vaginal opening and narrower along an opposite surface corresponding to the posterior of the vaginal opening to guide the patient as to the proper orientation for insertion. In certain embodiments, the proximal end of the insertion tube further comprises a plurality of exterior ribbed gripping surfaces proximal to the insertion shield. In certain embodiments, the proximal end of the insertion tube has a diameter greater than the distal end of the insertion tube.

In certain embodiments, the device of the present invention further comprises a handle retaining cover having a proximal end, a distal end, and comprising an insertion tube engaging surface, a cervical aligning tool engaging surface, and a cellular sampling tool engaging surface. In certain embodiments, the handle retaining cover is removably engageable with the device such that relative movement of the cervical aligning tool and the cellular sampling tool within the insertion tube is impeded until the handle retaining cover is physically removed by the user.

The present invention further provides a method of collecting a cervical and/or vaginal tissue sample from a patient using the device of the present invention. The inventive method comprises the steps of (a) inserting into the vagina of the patient a device of the present invention; (b) advancing the U-Ring of the cervical aligning tool distally from within the insertion tube in the first position to the second position for cervical cap alignment to engage the posterior cervical fornix of the patient; (c) moving the elongated cellular sampling tool distally from the first position to the second position for cervical cell tissue sampling; (d) rotating the cellular sampling tool, preferable two full rotations in each direction (clockwise and counter-clockwise), to capture cervical cell tissue at or within the patient's os onto the cellular adhesion surface; (e) moving the elongated cellular sampling tool proximally from the second position to the first position to shield the cervical tissue sample within the insertion tube; and (f) withdrawing the device from the vagina of the patient. In certain embodiments, the method also comprises the additional step, after step (a), of selectively disengaging a retaining mechanism on the device for user dependent release of the cervical aligning tool and/or the cellular sampling tool, such as by removing the handle retaining cover, or in alternative embodiments depressing a release lever.

In certain embodiments, the inventive method further comprises the later steps of either removing cervical tissue from the cellular adhesion surface by rinsing in a preservative solution, or separating the cellular adhesion surface from the cellular sampling tool; and placing the cellular adhesion surface or the cells thereon in a container of cellular preservative for storage and transportation to a laboratory for analysis.

The present invention further provides a kit for cervical cell tissue sampling comprising the device of the present invention, a resealable container of cellular preservative shaped to receive the cellular sampling tool cellular adhesion surface or the cells therein, and instructions for use of the device to obtain a cervical tissue sample and preserve the sample in the container. In certain embodiments, the kit further comprises a plurality of replacement cellular adhesion surfaces (e.g., brushes) and a plurality of containers of cellular preservative.

BRIEF DESCRIPTION OF THE DRAWINGS

Figure 1A:
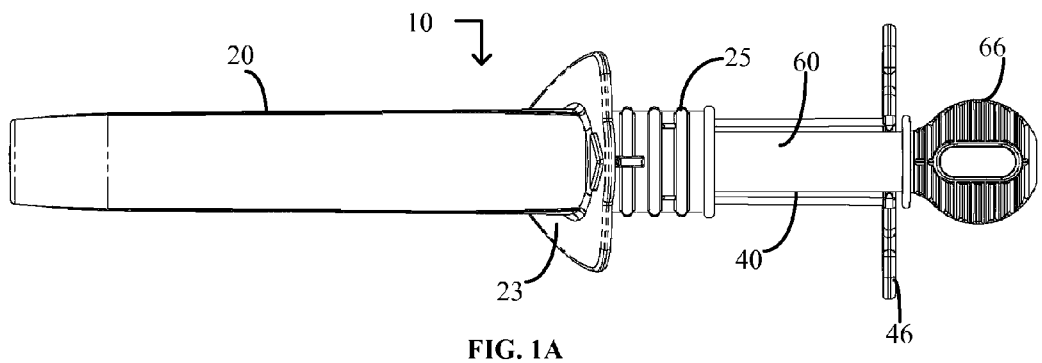

Having thus described various embodiments of the invention in general terms, reference will now be made to the accompanying drawings:

FIG. 1A shows an overhead/top view of the cervical cell tissue self-sampling device, according to one embodiment of the present invention.

Figure 1B:
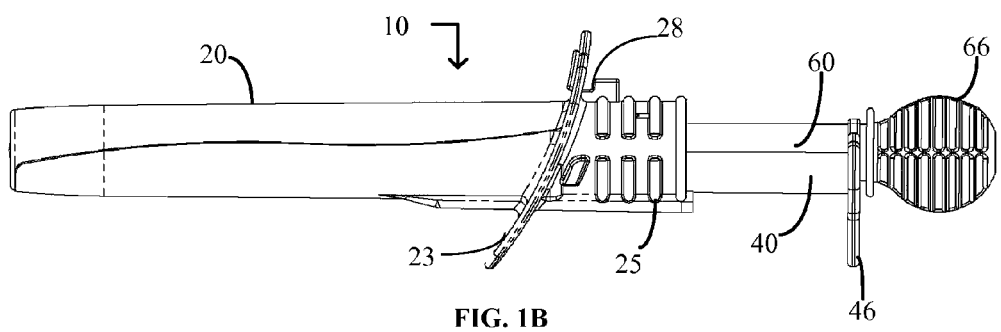

FIG. 1B shows a side view of the cervical cell tissue self-sampling device, according to one embodiment of the present invention.

Figure 1C:
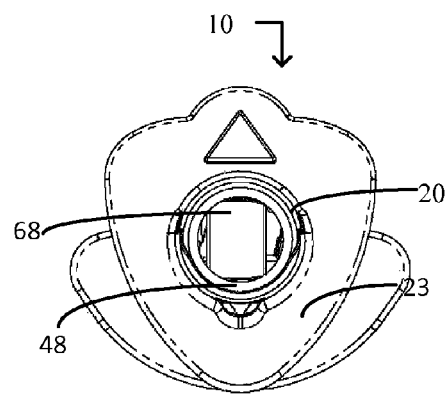

FIG. 1C shows a proximal end view of the cervical cell tissue self-sampling device, according to one embodiment of the present invention.

Figure 2A:
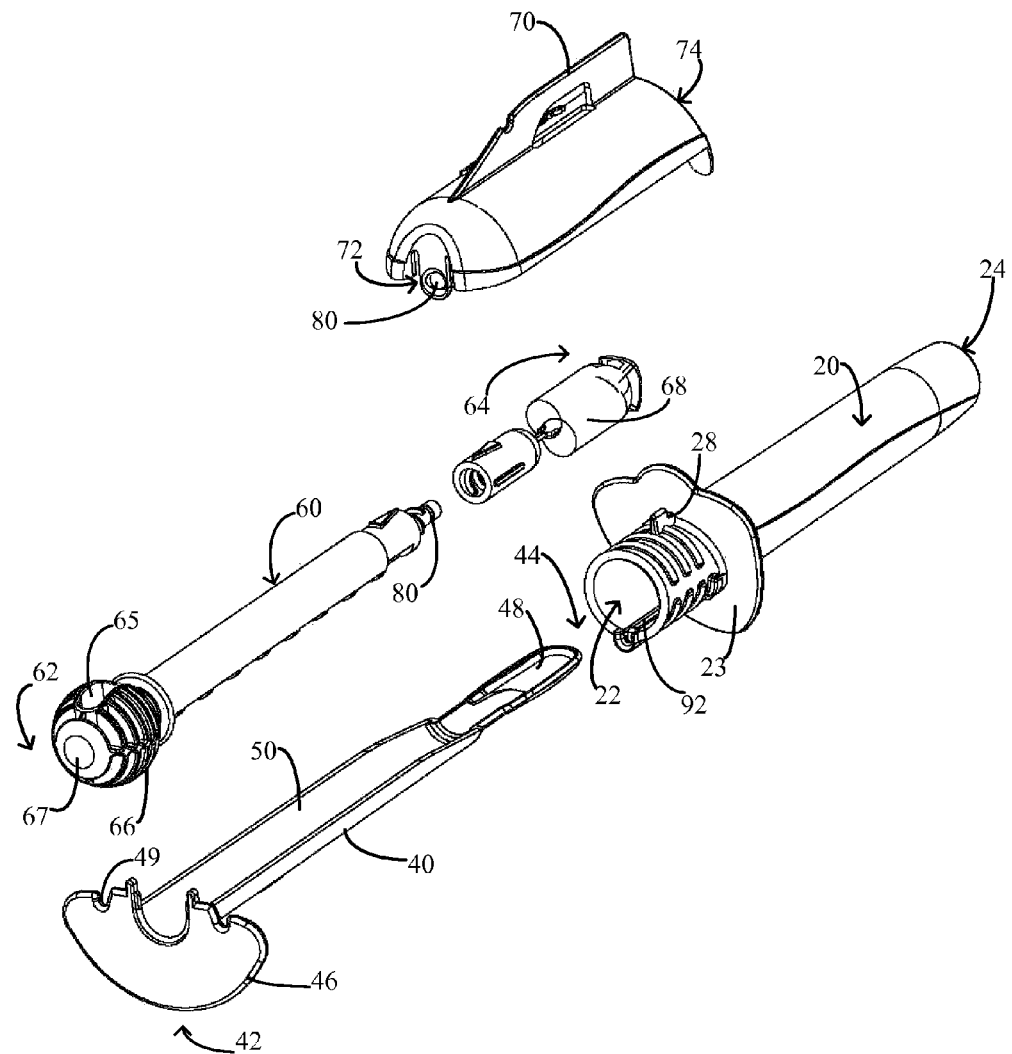

FIG. 2A shows an exploded top proximal perspective view of the cervical cell tissue self-sampling device with each component disassembled, according to one embodiment of the present invention.

Figure 2B:
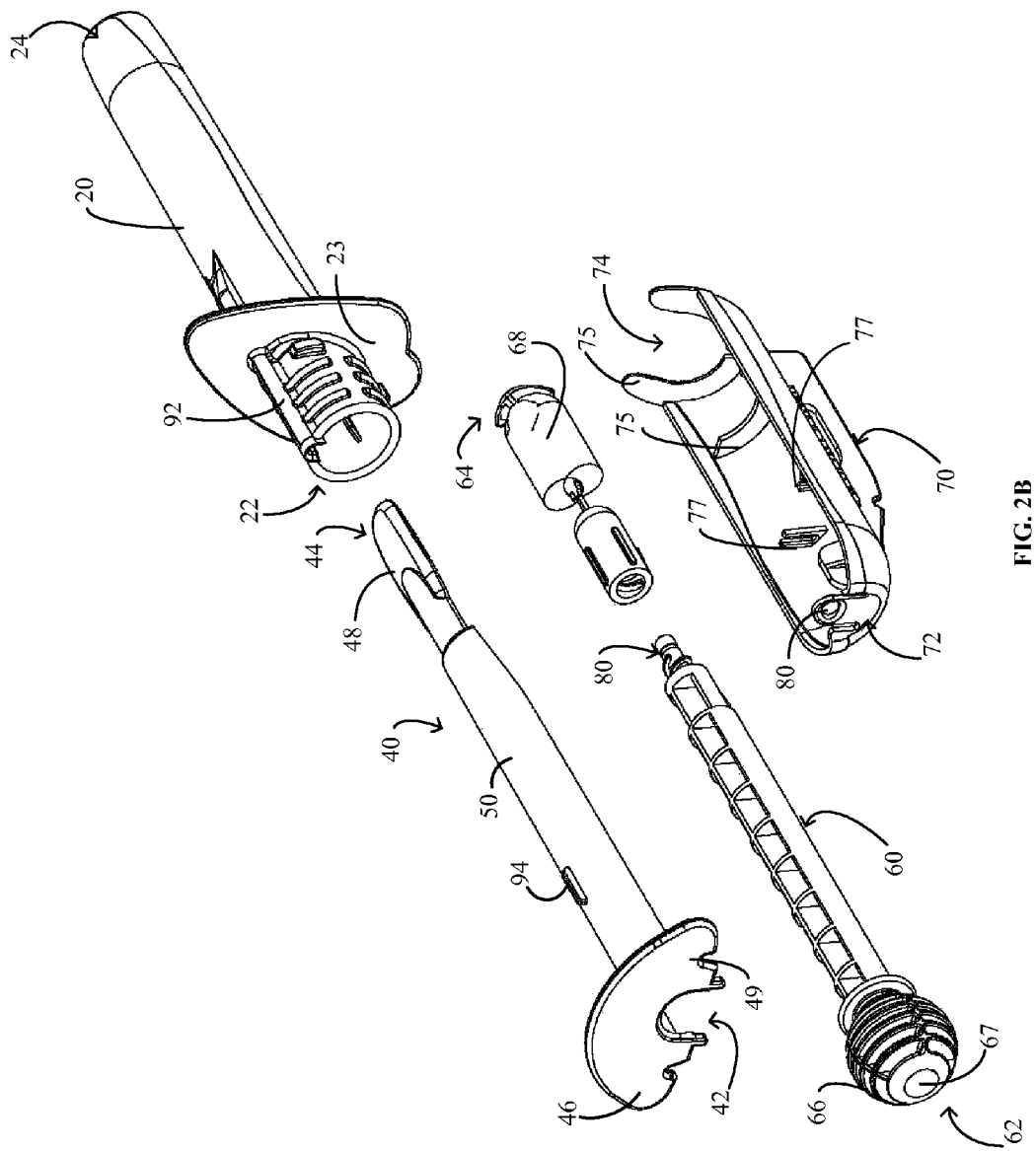

FIG. 2B shows an exploded bottom proximal perspective view of the cervical cell tissue self-sampling device with each component disassembled, according to one embodiment of the present invention.

Figure 2C:
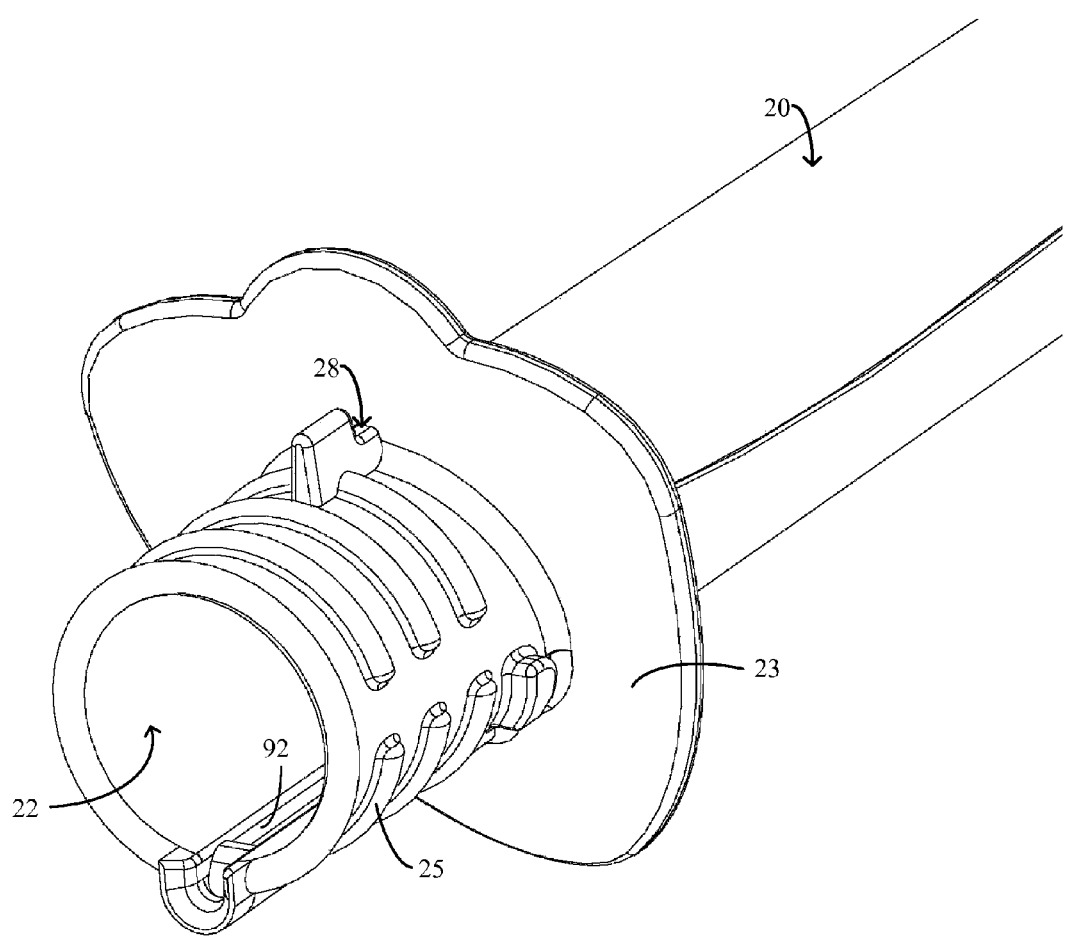

FIG. 2C shows a detailed top proximal perspective view of the proximal end of the insertion tube, according to one embodiment of the present invention.

Figure 3A:
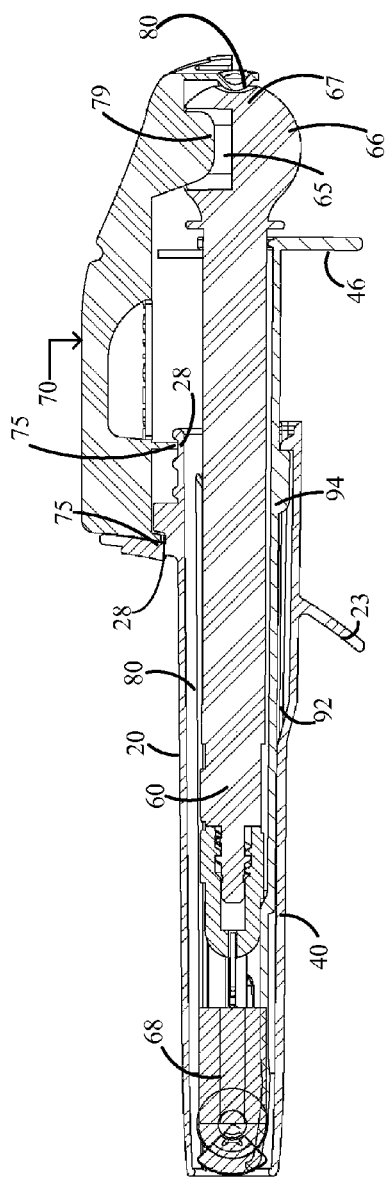

FIG. 3A shows a longitudinal cross-sectional view of the cervical cell tissue self-sampling device in an insertion position with a handle retaining cover attached thereto, according to one embodiment of the present invention.

Figure 3B:
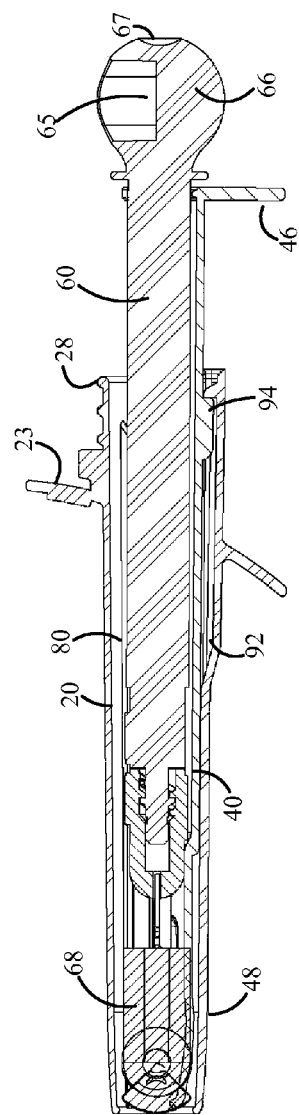

FIG. 3B shows a longitudinal cross-sectional view of the cervical cell tissue self-sampling device with the handle retaining cover disengaged, according to one embodiment of the present invention.

Figure 3C:
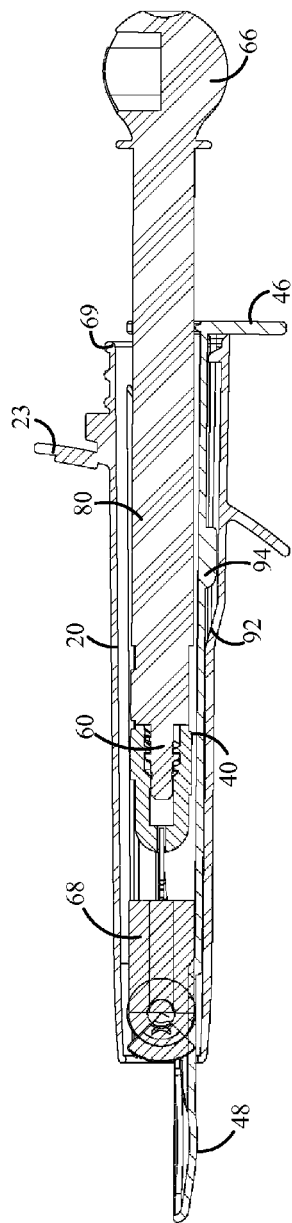

FIG. 3C shows a longitudinal cross-sectional view of the cervical cell tissue self-sampling device, in which the alignment tool is extended for cervical distension, according to one embodiment of the present invention.

Figure 3D:
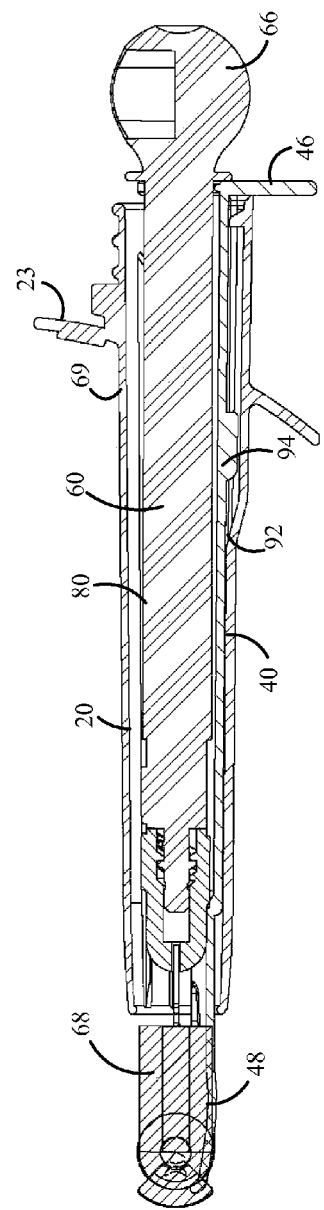

FIG. 3D shows a longitudinal cross-sectional view of the cervical cell tissue self-sampling device, in which the alignment tool and the tissue cellular adhesion surface are extended into position for collection of cervical tissues, according to one embodiment of the present invention.

Figure 4A:
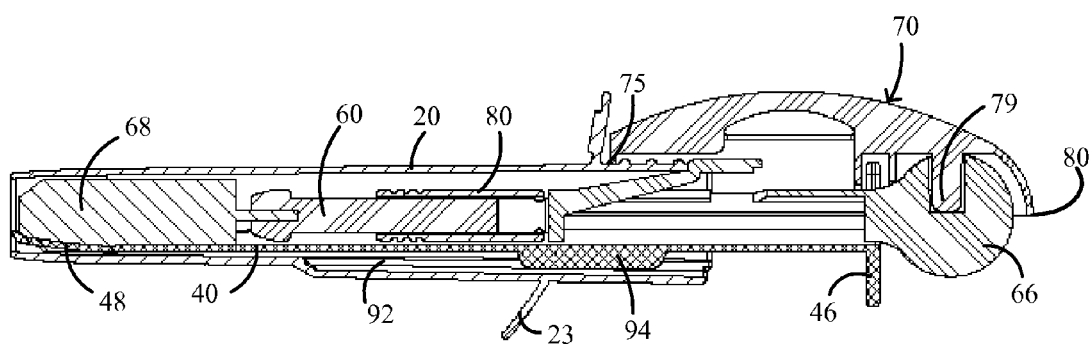

FIG. 4A shows a longitudinal cross-sectional view of the cervical cell tissue self-sampling device in an insertion position with a handle retaining cover attached thereto, according to another embodiment of the present invention.

Figure 4B:
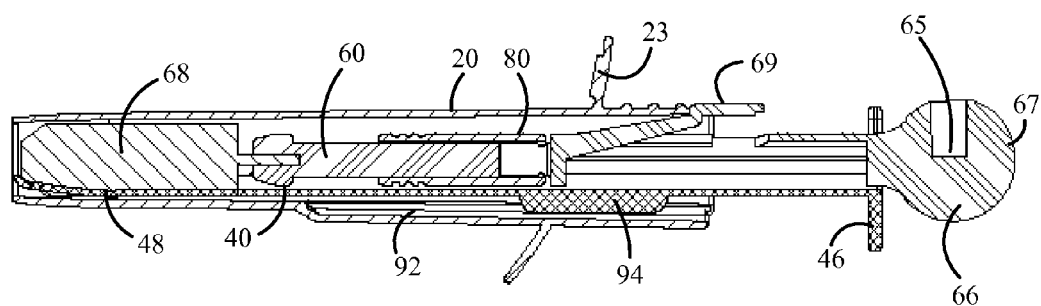

FIG. 4B shows a longitudinal cross-sectional view of the cervical cell tissue self-sampling device with the handle retaining cover disengaged, according to one embodiment of the present invention.

Figure 4C:
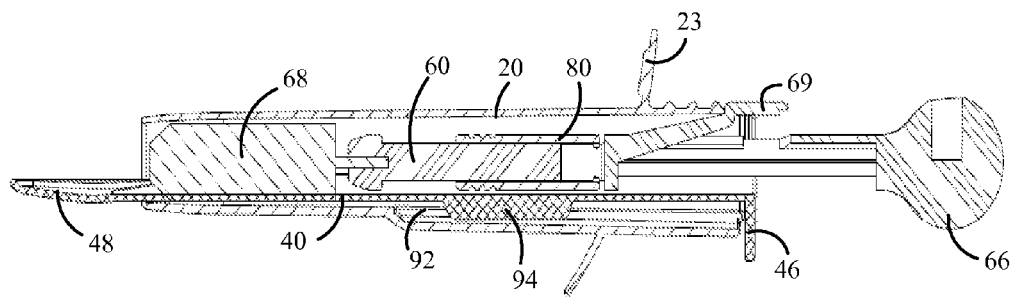

FIG. 4C shows a longitudinal cross-sectional view of the cervical cell tissue self-sampling device, in which the alignment tool is extended for cervical distension, according to one embodiment of the present invention.

Figure 4D:
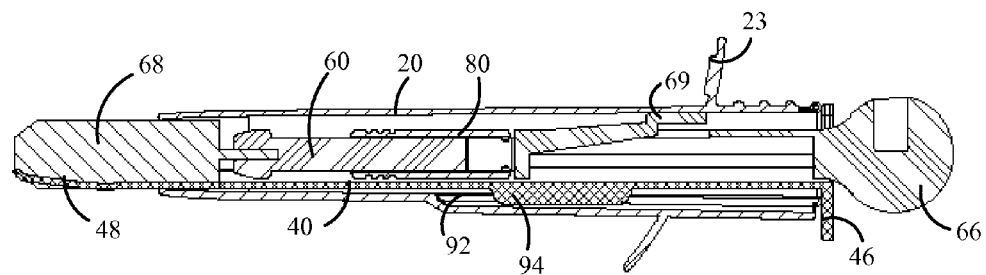

FIG. 4D shows a longitudinal cross-sectional view of the cervical cell tissue self-sampling device, in which the alignment tool and the tissue cellular adhesion surface are extended into position for collection of cervical tissues, according to one embodiment of the present invention.

Figure 5A:
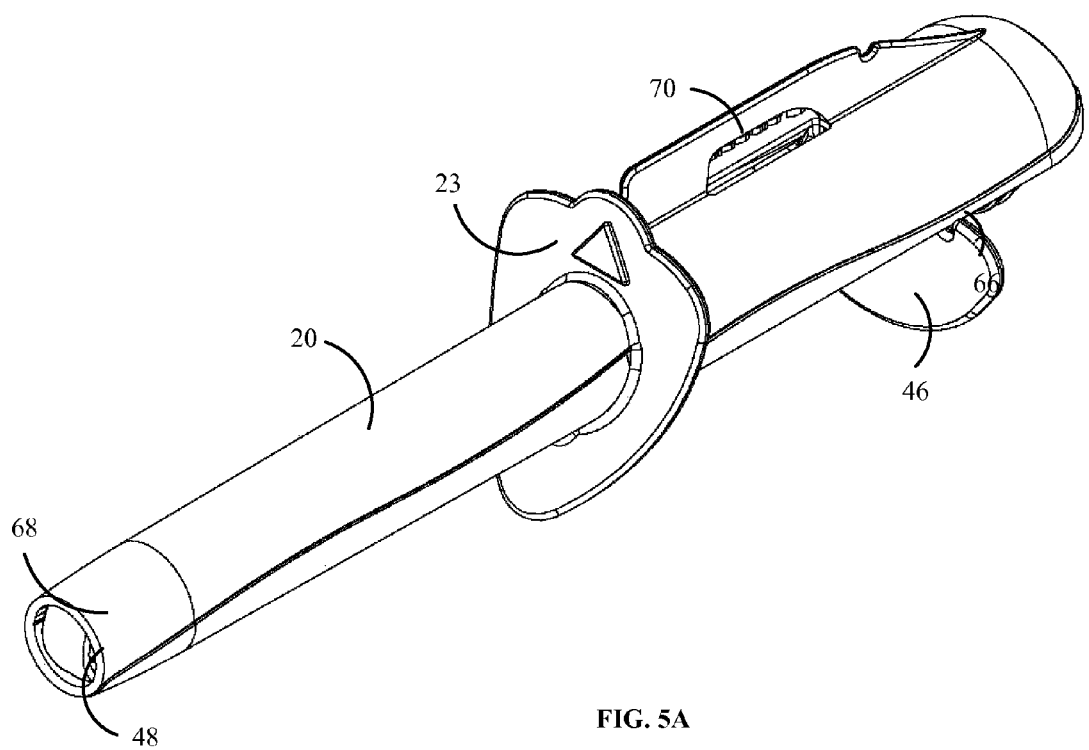

FIG. 5A shows a perspective top distal view of the cervical cell tissue self-sampling device in an insertion position with the handle retaining cover attached thereon, according to one embodiment of the present invention.

Figure 5B:
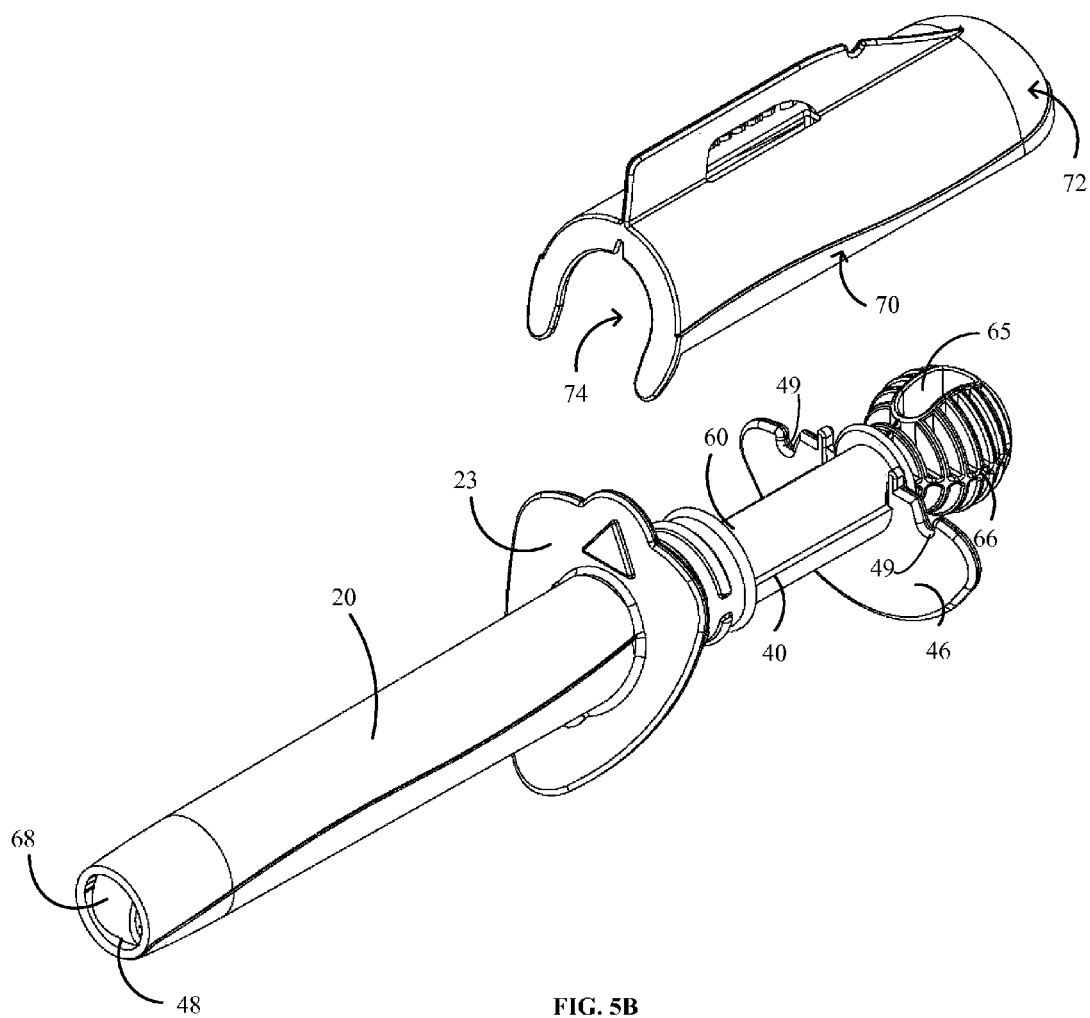

FIG. 5B shows a perspective top distal view of the cervical cell tissue self-sampling device with the handle retaining cover disengaged, according to one embodiment of the present invention.

Figure 5C:
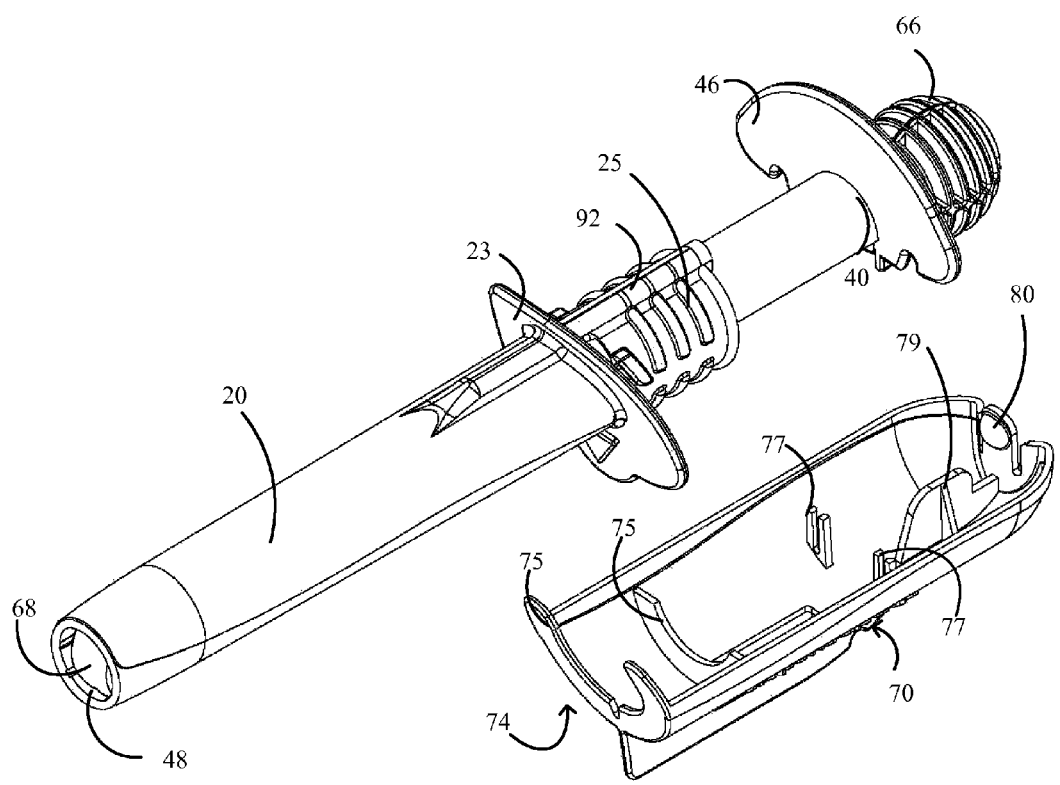

FIG. 5C shows a perspective bottom distal view of the cervical cell tissue self-sampling device with the handle retaining cover disengaged, according to one embodiment of the present invention.

DETAILED DESCRIPTION OF THE INVENTION

It is to be understood that the invention is not limited in its application to the details of construction and the arrangement of components set forth in the following description or illustrated in the drawings.

The present invention provides a cervical cell tissue self-sampling device, and method of use thereof, that can be self-administered by a female at any location including in the privacy of her own home. The inventive device and method of self-administration and collection of vaginal cervical tissue samples provide an efficient tool for privately performing a vaginal tissue sample collection for a Pap smear test without the assistance of a gynecologist or other medical practitioner. While reference to cervical cell tissue sampling for a Pap smear test is repeated herein, one of skill in the art will appreciate that the various embodiments of the device can be used for sampling various vaginal tissues and fluids upon which any diagnostic test of interest may be conducted. While the device is primarily intended to be used by the patient herself, the device can also be used by a nurse, gynecologist or any assisting medical practitioner on the patient, if so desired.

In certain embodiments, the present invention provides a device for collecting a cervical tissue sample from a patient comprising an elongated insertion tube shaped for insertion into the vagina of the patient. The insertion tube has a proximal end, a distal end, an exterior surface and an interior surface extending therethrough defining a passage. In certain embodiments, the insertion tube has a diminishing cross-sectional diameter from proximal end to the distal end for ease of insertion. The insertion tube is preferably round in a lateral cross-section, however, may also be any other shape, such as ovular, octagonal, or irregular, but which avoids any sharp angles or uncomfortable edges.

The elongated insertion tube can have a length for example in the range of about 100-220 mm, and an outer diameter that is flared from a smaller distal diameter in the range of about 10-20 mm to a larger proximal diameter in the range of about 30-50 mm. In certain embodiments, the elongated insertion tube has a length of about 100 mm, 120 mm, 140 mm, 160 mm, 180 mm, 200 mm, or 220 mm, and has an outer diameter of about 10 mm, 15 mm, 20 mm, 25 mm, 30 mm, 35 mm, 40 mm, 45 mm, or 50 mm. It will be understood and appreciated by those skilled in the art that the present invention encompasses various insertion tubes with variable lengths and outer diameters that are suitable for use for different female patients of different sizes.

The elongated insertion tube, as well as some of the other components can be made from medical-grade thermoplastics, evidencing the following desired characteristics: cost effectiveness; lightweight; strength; dimensional stability; low coefficient of friction/inherent lubricity; soft touch; and dye-dopable. Examples include: High-density Polyethylene (HDPE); High-density Polypropylene (HDPP); Polytetrafluoroethylene (PTFE, i.e., TEFLON®); and rigid Polyvinyl Chloride (PVC). The insertion tube is non-foldable in use, meaning that in normal use under forces applied by hand it will not collapse, flatten, or fold in on itself, but flexibility and cushioning can be provided. The insertion tube of the present invention can also be surface coated with any materials as needed by the patient, such as vaginal lubricants (e.g., KY®) that help insertion, disposed thereon when the device is made, or prior to insertion.

The device further comprises an elongated cervical aligning tool shaped for insertion and movement within the passage of the insertion tube. The cervical aligning tool has a proximal end with a U-shaped handle thereon, a distal end with a cervical aligning probe thereon, and a body therebetween. The cervical aligning tool handle may be referred to as the "U-Ring" herein for convenience, but it is understood that the handle is not necessarily U-shaped in the claimed embodiments. U-Ring is disposed outside the proximal passage of the insertion tube and can be manipulated by the hand of the user such that the aligning tool is movable between a first position for insertion, wherein the distal cervical aligning probe is contained and protected from the patient within the passage of the insertion tube, and a second position for cervical cap alignment, wherein the distal cervical aligning probe extends distally from the passage of the insertion tube to engage the cervical fornix of the patient to distend the cervix for exposure of the os for optimum cervical cell tissue sampling.

The body of the cervical aligning tool placed and movable inside the passage of the insertion tube preferably has a length longer than the insertion tube. In certain embodiments, the length of the body of the cervical aligning tool can be about 120 mm, 140 mm, 160 mm, 180 mm, 200 mm, 220 mm, or 240 mm. The outer size of the body of the cervical aligning tool is also smaller than the inner diameter of the insertion tube so that the body of the cervical aligning tool can move longitudinally from one position to another position within the insertion tube. In certain embodiments, the length of the cervical aligning probe is about 5 mm, 10 mm, or 15 mm. It will be understood and appreciated by those skilled in the art that the lengths and sizes of the cervical aligning tools correspond to the relative lengths and sizes of the insertion tubes used in the present invention. It will also be understood and appreciated by those skilled in the art that all or part of the cervical aligning tool may be constructed of any acceptable materials, such as medical grade thermoplastics and/or other polymer materials, similar to or different from the materials used for constructing the insertion tube.

The device further comprises an elongated cellular sampling tool shaped for insertion within the passage of the insertion tube and adjacent to or upon a portion of the body of the elongated aligning tool. In certain embodiments, the cervical cellular sampling tool is at least partially disposed within the advancing U-Ring of the cervical alignment tool. The sampling tool has a proximal end with an advancing handle thereon for manipulation by the hand of the user, and a distal end with a cellular adhesion surface thereon, such as a brush described in more detail below. The advancing handle, which may be ball-shaped, extends from the proximal passage of the insertion tube proximal to the U-Ring of the aligning tool.

The movement of the cervical aligning tool and/or the cellular sampling tool can be dependent upon the release of a retaining mechanism by the direct or indirect action of the patient or other person using the device. The cellular sampling tool is dependently movable between a first position for insertion wherein the distal cellular adhesion surface is contained within the passage of the insertion tube, and a second position for cervical cell tissue sampling wherein the distal cellular adhesion surface extends distally from the passage of the insertion tube. Dependency of the movement of the cellular sampling tool can be subject to direct manual disengagement of a retaining mechanism to decouple the sampling tool from the insertion tube or cervical alignment tool, or such as when a handle retaining cover is removed, or indirectly through automatic engagement or disengagement of a mechanism to decouple the sampling tool from the insertion tube or cervical alignment tool when the alignment tool is moved into the second position.

The body of the cellular sampling tool placed and movable inside the passage of the insertion tube preferably has a length longer than the cervical aligning tool and the insertion tube. In certain embodiments, the length of the body of the cellular sampling tool can be about 125 mm, 140 mm, 160 mm, 180 mm, 200 mm, 220 mm, or 250 mm. The outer size of the body of the cellular sampling tool is also smaller than the inner diameter of the insertion tube so that the body of the cellular sampling tool can move longitudinally from one position to another position within the insertion tube. In certain embodiments, the length of the cellular adhesion surface is about 5 mm, 10 mm, or 15 mm. It will be understood and appreciated by those skilled in the art that the lengths and sizes of the cellular sampling tools correspond to the relative lengths and sizes of the insertion tubes used in the present invention. It will also be understood and appreciated by those skilled in the art that all or part of the cellular sampling tool may be constructed of any acceptable materials, such as medical grade thermoplastics and/or other polymer materials, similar to or different from the materials used for constructing the insertion tube or cervical aligning tool.

As mentioned, the movement of the cellular sampling tool is dependent as shown in several different exemplary embodiments of the invention, each intended to, among other things, protect the patient's vaginal tissue and protect the cellular adhesion surface from premature contact with the vaginal walls or cervix until the user has inserted the device to the appropriate vaginal canal depth. In some embodiments, the distal movement of the cellular sampling tool is dependent upon prior distal movement of the cervical alignment tool to expose the os, and to protect the posterior of the sampling tool from vaginal contamination, for optimum cervical cellular sampling. In certain embodiments, the distal movement of the cellular sampling tool is dependent upon the patient manually disengaging a retaining mechanism comprising a release tab on the cellular sampling tool in selective communication with the insertion tube. In other embodiments, distal movement of the cellular sampling tool is dependent upon removing a retaining mechanism comprising a protective handle retaining cover which engages the tube, aligning tool and/or sampling tool until manually removed by the user. In other embodiments, the distal movement of the cellular sampling tool is dependent upon the patient disengaging the sampling tool from a fixed position relative to the aligning tool by moving the aligning tool into the second position within the tube, which automatically releases a biased release pin or tab to permit movement of the sampling tool.

In other embodiments, the cellular sampling tool is rotatable along the longitudinal axis of the elongated device through any portion thereof within the insertion tube and bearing upon the cervical aligning tool and U-Ring shaped handle. In certain embodiments, the cellular adhesion surface is an abrasive brush element. In certain embodiments, the distal end of the brush element has a cone-shaped distal end. In certain embodiments, the cellular adhesion surface is separable from the cellular sampling tool, and may be replaced with a fresh cellular adhesion surface for re-use of the device. The cellular adhesion surface can be manually connected and separated from the remainder of the sampling tool at a union by any mechanism such as disengaging a pin and slot combination, or a threaded and/or frictional snapping engagement.

In certain embodiments, the cellular sampling tool further comprises a retaining sleeve slidably disposed upon the sampling tool between a first position for retaining the adhesion surface by encompassing the union to prevent unintended disengagement, and a second position for releasing the adhesion surface by exposing the union to permit disengagement.

In certain embodiments, the cellular adhesion surface on the distal end of the cellular sampling tool is a brush element. In certain embodiments, the brush element is cone-shaped, however, any shape that will serve to gently release cellular tissue from the cervix and os will work. In certain embodiments the brush element is constructed from a twisted wire pair having polymer bristles extending therefrom, as is known in the art. In certain embodiments, the twisted wire pair extends distally, then makes a 360° loop before returning proximally to maximize the density of bristles on the distal end. The density of bristles on the distal end of the brush can be 2-3 times, or more, greater than the density of bristles in the more proximal portion. The brush element acts to gently exfoliate and adhere cervical cells thereto. An off-axis orientation of the brush element can bias the brush toward the cervix with the cellular sampling tool oriented with the advancing handle. The cellular sampling tool can have a length which is sufficient to extend to the cervix of the vagina, and is actuatable by the user from outside the vaginal canal to contact the cervix preferably at the os to collect a cellular specimen. Cellular specimens are typically collected by rotating the brush element at or within the os 1 to 5 times in one direction, and then rotating the brush element at or within the os 1 to 5 times in the other direction, or any combination of the above. Cellular exfoliating motion can also be imparted by gently inserting and withdrawing the brush element back and forth several times before, during or after rotation.

Brush bristles of the cellular adhesion surface are preferably made from common, synthetic polymer fibers, evidencing the following desired/relevant characteristics: cost effectiveness, good balance between flexibility for form-fitting in and around unique contours and rigidity for ultimate surface friction, ability to create micro-abrasive/scaly surface texture for more effective specimen dislodging/exfoliation/removal, and trapping/retention of cellular samples thereon. The following cellular adhesion bristle parameters can also be adjusted: round vs. rectangular vs. diamond-shaped vs. hexagonal bristle cross-section; rounded vs. blunt vs. pointed bristle tip; embossed vs. feathered vs. coated bristle shaft; wavy (for bushier brush head) vs. straight bristle shaft. Material examples include: Nylon, Polyethylene, Polypropylene, and DuPont's HEROX® and TYNEX®.

When used in construction the brush wire can be made from medical/surgical-grade polymer or stainless steel; specifically, chosen from the austenitic steel family, for example, Type 302 or 304 stainless steel. The brush wire can be, for example, in a twisted-wire, closed loop configuration, so as not to expose any rough-cut ends or a blunt point, which could cause sensitive tissue trauma, and attendant pain, bruising, bleeding, or infection. The closed loop may present a rounded and benign tip which simply and atraumatically collapses into itself, if inadvertently pushed too hard against the anatomy. Optimization variables include: wire gauge and chemical treatments for strength, flexibility, and durability; single stem/single spiral vs. double stem/single spiral vs. double stem/double spiral configurations to control bushiness and flexibility; and spirals per inch also to control bushiness or bristle density.

In certain embodiments, the cervical aligning probe is spoon-shaped having a smooth edged convex curvature concentric with the distal end of the insertion tube. The probe can be any shape to engage the posterior cervical fornix to align and distend the cervix without puncturing or scratching tissue. In other embodiments, the cervical aligning tool further comprises an aligning extension element extending along a portion of the body which engages an elongated alignment groove extending from the interior surface of the insertion tube. The alignment system can alternatively be any configuration of articulating surfaces which prevents the aligning tool from rotating within the insertion tube to avoid misdirecting the aligning probe upon advancement from the insertion tube. In certain embodiments the elongated alignment groove comprises a shallower portion near the proximal end to alert the user when the aligning tool is within that region by friction with the extension element, analogous to a "speed bump" to prevent unintentional removal of the cervical aligning tool from the insertion tube.

In certain embodiments, the U-Ring of the cervical aligning tool engages the proximal portion of the passage of the insertion tube as a stop point to impede further distal movement of the cervical aligning tool within the vagina. In certain embodiments, the advancing handle of the cellular sampling tool engages the proximal portion of the U-Ring of the cervical aligning tool as a stop point to impede further distal movement of cellular sampling tool within the vagina.

In certain embodiments, the proximal end of the insertion tube further comprises an annular insertion shield peripherally extending from the exterior surface to impede insertion within the vagina beyond a predetermined depth. In certain embodiments, the annular insertion shield extends in a generally triangular shape, being wider along a surface corresponding to the anterior of the vaginal opening and narrower along an opposite surface corresponding to the posterior of the vaginal opening to guide the patient as to the proper orientation for insertion. In certain embodiments, the proximal end of the insertion tube further comprises a plurality of exterior ribbed gripping surfaces for the user to hold the tube proximal to the insertion shield. In certain embodiments, the proximal end of the insertion tube has a diameter greater than the distal end of the insertion tube for ease of insertion.

In certain embodiments, the device of the present invention further comprises a sampling tool release mechanism comprising a handle retaining cover having a proximal end, a distal end, and comprising at least one insertion tube engaging surface, at least one cervical aligning tool engaging surface, and at least one cellular sampling tool engaging surface, wherein the handle retaining cover is removably engageable onto the device such that movement of the cervical aligning tool and the cellular sampling tool relative to one another, and/or relative to the insertion tube, is impeded until the handle retaining cover has been removed.

The present invention further provides a method of collecting a cervical and/or vaginal tissue sample from a patient using the device of the present invention. The method comprises the steps of (a) inserting into the vagina of the patient a device of the present invention; (b) disengaging a handle retaining mechanism to permit distal movement of the cervical aligning tool and the cellular sampling tool, (c) advancing the handle of the cervical aligning tool distally from within the insertion tube in the first position to the second position for cervical cap alignment to engage the cervical fornix of the patient; (d) moving the elongated cellular sampling tool distally from the first position to the second position for cervical cell tissue sampling; (e) rotating the cellular sampling tool to capture cervical tissue at the patient's os on the cellular adhesion surface; (f) moving the elongated cellular sampling tool proximally from the second position to the first position to shield the cervical tissue sample within the insertion tube; and (g) withdrawing the device from the vagina of the patient. In certain embodiments, the inventive method further comprises the later steps of separating the cellular adhesion surface from the cellular sampling tool; and placing the cellular adhesion surface in a container of cellular preservative. In certain embodiments, the method provides for performing step (c) prior to step (b), where the handle retaining mechanism prevents distal movement of only the cellular sampling tool until it is disengaged.

Therefore, in certain embodiments the inventive method comprises a step of selectively actuating the device for dependent deployment of the cervical cap alignment sampling tool or cervical sampling tool, by engaging or disengaging a handle retaining mechanism. In various embodiments, the handle retaining mechanism is disengaged by removing a handle retaining cover element, or depressing a release button when present, before advancing the sampling tool. In certain embodiments, movement of the cervical alignment tool into the distal position will automatically trigger a release mechanism, such as a biased pin, to permit the sampling tool to move distally.

In certain embodiments, cellular specimens are collected by rotating the cellular sampling tool at or within the os 1 to 5 times, or 2 to 3 times, in one direction, and then rotating the cellular sampling tool at or within the os 1 to 5 times, or 2 to 3 times, in the other direction, or any combination of the above. Cellular exfoliating motion can also be imparted by gently inserting and withdrawing the cellular sampling tool back and forth several times before, during or after rotation.

The present invention further provides a kit for cervical cell tissue sampling comprising the device of the present invention, a resealable container of cellular preservative shaped to receive the cellular sampling tool cellular adhesion surface or cellular sample therein, and instructions for use of the device to obtain a tissue sample and preserve the sample in the container. In certain embodiments, the kit further comprises a plurality of replacement cellular adhesion surfaces; and a plurality of containers of cellular collection media.

The collection media is biologic preservative selected based on the desired sample testing to be performed. The collection media is suitable for preserving and transporting human tissue cells and related tissue secretions, for example, PRESERVCYT® from Cytyc Corporation (Foxboro, Mass.), SUREPATH® Perservative Solution from TriPath Imaging Inc. (Burlington, N.C.), and CYTORICH® from Thermo Scientific division of Thermo Fisher Scientific, Inc. (Waltham, Mass.). To test for high-risk human Papillomavirus (HPV), chlamydia (CT) and gonorrhea (GC), the collection medium can be the RAPID CAPTURE® System specimen transport medium (STM) from Digene Corporation (Gaithersburg, Md.).

Therefore, the present invention provides a vaginal cervical cell tissue self-sampling device and method of self-administration for collecting cervical tissue cells for medical testing, such as for Pap smear or cervical cancer screening. The device primarily comprises an insertion tube, within which is carried a movable cervical aligning tool with an aligning probe (e.g., aligning spoon) on its distal end, and a separately movable cellular sampling tool with a cellular adhesion surface (e.g., a nested brush tool) on its distal end. The brush tool of the cellular adhesion surface can be dependently movable forward along the aligning tool by the user. In one embodiment, the cellular sampling tool is movable relative to the aligning tool dependent upon election by the user to selectively disengage a retaining mechanism. In one embodiment, the aligning spoon must first have been extended to the predetermined length through the insertion tube to automatically disengage a biased pin retaining the cellular sampling tool for movement by the user. In one embodiment, the cellular sampling tool must first have been selectively released from engagement with a retaining cover for movement by the user. In another embodiment, the aligning tool must first have been selectively released from engagement with a retaining cover for movement by the user.

Referring generally to FIGS. 1-5 of the drawings according to various embodiments of the present invention, the cervical and/or vaginal tissue self-sampling device (10) generally includes an elongated insertion tube (20), an elongated cervical aligning tool (40) with a U-shaped handle ("U-Ring") (46) attached to its proximal end (42), and an elongated cellular sampling tool (60) with a cellular adhesion surface (68) attached to its distal end (64), with an advancing handle (66) attached to its proximal end (66).

The elongated insertion tube (20) is shaped for insertion into the vagina of the patient, and has a proximal end (22), a distal end (24), an exterior surface and an interior surface extending therethrough defining a passage, where the body of the elongated aligning tool (40) with the advancing U-Ring (46) is placed. In certain embodiments, the proximal end (22) of the insertion tube (20) further comprises an annular insertion shield (23) peripherally extending from the exterior surface to impede insertion of the device (10) within the vagina beyond a predetermined depth (See FIGS. 1A and 1B, FIGS. 2A and 2B). The annular insertion shield (23) is shown as triangular in shape extending wider along a surface corresponding to the anterior of the vaginal opening and narrower along an opposite surface corresponding to the posterior of the vaginal opening to guide the patient as to the proper orientation for insertion (See FIGS. 1A and 1B, FIGS. 2A and 2B). In certain embodiments, the proximal end (22) of the insertion tube (20) further comprises a plurality of exterior ribbed gripping surfaces (25) proximal to the insertion shield (23) (See FIGS. 1A and 1B, FIGS. 2A and 2B). In certain embodiments, the proximal end (22) of the insertion tube (20) has a diameter greater than the distal end (24) of the insertion tube (20).

According to one embodiment of the present invention, the elongated cervical aligning tool (40) has a proximal end (42) with a U-Ring (46) thereon, a distal end (44) with a cervical aligning probe (48) thereon, and a body (50) therebetween, wherein the U-Ring (46) is disposed outside the proximal passage of the insertion tube (20) and is movable between a first position for insertion wherein the distal cervical aligning probe (48) is contained within the passage of the insertion tube (20), and a second position for cervical cap alignment wherein the distal cervical aligning probe (48) extends distally from the passage of the insertion tube (20) to engage the cervical fornix of the patient (See FIGS. 2A, 2B, 3B and 3C).

In certain embodiments, the cervical aligning probe (48) is spoon-shaped having a convex curvature concentric with the distal end of the insertion tube (20) (See FIGS. 2A and 3C). It will be understood and appreciated by those skilled in the art that the cervical aligning probe can be in any other shapes avoiding sharp corners or points. In other embodiments, the cervical aligning tool (40) further comprises an aligning extension element (94) extending along a portion of the body which engages an elongated alignment groove (92) extending from the interior surface of the insertion tube (20) (See FIGS. 2A and 2B). The U-Ring (46) of the cervical aligning tool (40) engages the proximal portion of the passage (30) of the insertion tube (20) to impede further distal movement of the cervical aligning tool (40) within the vagina to a predetermined depth.

The cervical self-sampling device further comprises a cellular sampling tool (60) having a proximal end (62) with a ball-shaped advancing handle (66) thereon, a distal end (64) with a cellular adhesion surface (68) thereon, wherein the advancing handle (66) extends from the proximal passage of the insertion tube (20) proximal to the U-Ring (46) of the aligning tool (40), and is dependently movable between a first position for insertion wherein the distal cellular adhesion surface (68) is contained within the passage of the insertion tube (20), and a second position for cervical cell tissue sampling wherein the distal cellular adhesion surface (68) extends distally from the passage of the insertion tube (20) (See FIGS. 2A, 2B, 3B, and 3C).

In the embodiment shown in FIGS. 4A-4D, the distal movement of the cellular sampling tool (60) is dependent upon the patient disengaging a retaining mechanism comprising a release tab (69) on the cellular sampling tool (60) in selective communication with the insertion tube (20). The release tab (69) shown is a flexibly resilient flange of polymer material that can be depressed by the user to disengage away from the insertion tube (20) stopping point, however, a wide variety of alternatively biased or spring-loaded manual release mechanisms will be apparent to one of skill in view of the present disclosure. In other embodiments, not shown in the figures, the distal movement of the cellular sampling tool is dependent upon the patient selectively moving the aligning tool into the second position, for example, whereby the retaining mechanism comprising indentations on the interior surface of the tube which can engage one or more biased pins holding the alignment tool and sampling tool in a fixed relative position to automatically release when the alignment tool is distally inserted into the tube in the second position.

In addition to being movable in a distal direction for cervical cell tissue sampling, the cellular sampling tool (60) is rotatable within the insertion tube (20) and upon the cervical aligning tool (40) and U-Ring (46) cellular tissue can be retained on the bristles of the cellular adhesion surface (68) of the sampling tool (60) by rotating it several times against the os of the cervix. According to one embodiment of the present invention, the advancing handle (66) of the cellular sampling tool (60) engages the proximal portion of the U-Ring (46) of the cervical aligning tool (40) to impede further distal movement of cellular sampling tool (60) within the vagina.

In manufacturing assembly of the device, the cellular sampling tool (60) is placed upon the cervical aligning tool (40) with the advancing handle (66) extending proximal to the U-Ring (46) of the aligning tool (40). The combined cellular sampling tool (60) along with the cervical aligning tool (40) are placed inside the passage of the insertion tube (20). The handle (66) of the cellular sampling tool (60) along with the U-Ring (46) of the cervical aligning tool (40) are placed outside and proximal to the proximal end (22) of the insertion tube (20), where they are secured to the tube (20) by a handle retaining cover (70). The handle retaining cover (70) is intended to remain in place before and during insertion into the patient's vagina, and to be removed before the cervical aligning tool and cellular sampling tool are extended (See FIGS. 3A, 4A, and 5A showing the insertion position where the handle retaining cover is on, and FIGS. 3B, 4B, 5B, and 5C showing the handle retaining cover off). However, the retaining cover (70) can also be removed before insertion of the tube, or after distal movement of the aligning tool. In either case, distal movement of at least the cellular sampling tool (60) is dependent upon prior user removal of the retaining cover (70).

FIGS. 2B, 3A, 4A, and 5C show that in one embodiment, the device comprises a handle retaining mechanism comprising a handle retaining cover (70) having a proximal end (72), a distal end (74), and comprising an insertion tube engaging surface (75), cervical aligning tool engaging surfaces (77), and a cellular sampling tool engaging surfaces (79), (80), wherein the handle retaining cover (70) is removably engageable with the device (10) such that movement of the cervical aligning tool (40) and the cellular sampling tool (60) is impeded until the retaining cover (70) is lifted off the device (10) by the user. The sampling tool handle (66) has retaining cover engagement surfaces (65), (67) corresponding to the cellular sampling tool engaging surfaces (79), (80), respectively. The aligning tool has further engagement surfaces (49) on the top of the U-Ring. The insertion tube (20) has retaining tube engagement surfaces (28). In some embodiments, the cervical aligning tool (40) can move forward along these engagement surfaces (49), while the retaining cover is engaged, preventing the cellular sampling tool (60) from moving. The retaining cover is maintained in place by frictional contact between the elements due to sized tensioning, or flexibly biased tensioning, of the various engaging surfaces configured as desired to be retained. In particular, the proximal sampling tool handle engaging surface (80) indentation can provide the frictional contact tension of a magnitude to prevent the cover from falling off on its own, but to be readily removed by a single-handed action, and to be snapped back in to place when desired.

In certain embodiments such as those shown, the cellular adhesion surface (68) is separable from the cellular sampling tool (60) (See FIGS. 2A and 2B). In certain embodiments, the cellular sampling tool (60) further comprises a retaining element (80) disposed upon the sampling tool (60) between a first position for retaining the adhesion surface (68) and a second position for releasing the adhesion surface (68) (See FIGS. 2A and 2B). In certain embodiments, the retaining element is a threaded member that engages threads on the proximal end of the cellular adhesion surface. The invention thereby provides that the cervical tissue sample on the adhesion surface can be disengaged from the rest of the device for storage and transportation of the cellular sample to a laboratory for testing and analysis. In some embodiments, the cellular sample may be removed from the adhesion surface by rinsing in a cellular preservative solution, and in other embodiments, the entire adhesion surface can be stored with the cellular sample thereon within a container of cellular preservative solution. The invention also thereby provides for re-use of the main device with replacement adhesion surfaces, which can be provided in a kit or made available for individual purchase.

The present invention also provides methods of collecting a cervical tissue sample from a patient using the device of the present invention. The inventive method comprises the steps of (a) inserting into the vagina of the patient a device (10) of the present invention as shown in FIG. 3A or 4A; (b) advancing the U-Ring (46) of the cervical aligning tool (40) distally from within the insertion tube (20) in the first position to the second position for cervical cap alignment to engage the posterior cervical fornix of the patient as shown in FIG. 3C; (c) removing the handle retaining cover as shown in FIG. 3B, (d) moving the elongated cellular sampling tool (60) distally from the first position to the second position for cervical cell tissue sampling as shown in FIG. 3D; (e) rotating the cellular sampling tool (40) several times in each direction at and within the patient's os, and/or gently inserting and withdrawing the tool in the os, to capture cervical tissue on the cellular adhesion surface (68); (f) moving the elongated cellular sampling tool (60) and optionally the cervical cap alignment tool (40) proximally from the second position to the first position to shield the cervical tissue sample within the insertion tube (20); and (g) withdrawing the device (10) from the vagina of the patient.

In certain other methods, the insertion tube (20) is inserted into the vagina with the cervical aligning probe (48) (e.g., spoon) and cellular sampling adhesion surface (68) (e.g., brush element) fully retracted within the insertion tube (20) and secured in place with the handle retaining cover (70). When the insertion tube (20) has been inserted to the depth of the cervix, the handle retaining cover is removed. The cervical aligning probe (48) is then moved forward outside the distal end (24) of the insertion tube (20) and against the posterior fornix of the cervix, which distends the posterior side of the cervix away and exposes the cervical opening (the os) for the brush tip of the sampling adhesion surface (68) still inside the tube (See FIG. 4C). As shown in the embodiment of FIG. 4C, with the end of the aligning probe (48) fully extended outside the tube (20), the cellular sampling tool (40) can be released by the user depressing a release tab (69), to be advanced outside the distal end (24) of the insertion tube (20) over the aligning probe (48). Thus, the insertion tube (20) and aligning probe (48) have positioned the brush tip of the sampling adhesion surface (68) at or within the os, whereby endocervical cells of interest can be captured thereon by rotation and/or gentle plunging of the sampling tool (60).

After the specimens are collected, the sampling adhesion surface (68) and aligning probe (48) are withdrawn back into the protective tubing (20), and then the entire device (10) is withdrawn from the vaginal canal. The adhesion surface (68) with the cellular sample thereon can then be dipped into a container of cellular preservative and agitated to release the sample for shipping and further laboratory analysis. In other embodiments, the cellular adhesion surface (68) can be separated from the cellular sampling tool (60), such as by rotating the cellular adhesion surface (68) which can be placed entirely in a container of cellular preservative for shipping and further laboratory analysis. The device (10) can be cleaned and re-used.

The inventive device is intended to be provided in a kit with the insertion tube, cervical aligning tool, and cellular sampling tool assembled, as illustrated. The kit for cervical cell tissue sampling comprises the device of the present invention, a pharmaceutically acceptable vaginal lubricant, one or more resealable containers of cellular preservative shaped to receive the cellular adhesion surface therein, and instructions for use of the device to obtain a tissue sample and preserve the sample in the container for shipping and further laboratory analysis. In certain embodiments, the kit further comprises a plurality of replacement cellular adhesion surfaces and a plurality of containers of cellular preservative. After the user has collected the cervical tissue sample and placed it in the container of cellular preservative, the container is sent (such as by mail or courier) to a laboratory for analysis of the sample.

Although the invention has been described with a certain degree of particularity, it is understood and appreciated by those skilled in the art that the present disclosure has been made only by way of example. The device and the method of use thereof, of the present invention may be changed or modified using alternative mechanisms and materials known in the art without departing from the spirit and scope of the invention. Thus, the scope of the invention should not be limited by the foregoing specification, but rather, only defined in the following claims.

What is claimed is:

1. A device for collecting a cervical tissue sample from a patient comprising:
   (a) an elongated insertion tube shaped for insertion into the vagina of the patient and having a proximal end, a distal end, an exterior surface and an interior surface extending therethrough defining a passage;
   (b) an elongated cervical aligning tool shaped for insertion within the passage of the insertion tube and having a proximal end with a handle thereon, a distal end with a cervical aligning probe thereon and a body therebetween, wherein the aligning tool handle is disposed outside the proximal passage of the insertion tube and is movable between a first position for insertion wherein the distal cervical aligning probe is contained within the passage of the insertion tube, and a second position for cervical cap alignment wherein the distal cervical aligning probe extends distally from the passage of the insertion tube to engage the cervical fornix of the patient; and
   (c) an elongated cellular sampling tool shaped for insertion within the passage of the insertion tube, and having a proximal end with an advancing handle thereon, a distal end with a cellular adhesion surface thereon, wherein the advancing handle extends from the proximal passage of the insertion tube, and is movable between a first position for insertion wherein the distal cellular adhesion surface is contained within the passage of the insertion tube, and a second position for cervical cell tissue sampling wherein the distal cellular adhesion surface extends distally from the passage of the insertion tube.

2. The device of claim 1, wherein distal movement of the cellular sampling tool is released by a retaining mechanism comprising a handle retaining cover comprising a proximal end, a distal end, an insertion tube engaging surface, a cervical aligning tool engaging surface, and a cellular sampling tool engaging surface, wherein the handle retaining cover is removably disengageable with the device such that distal movement of the cervical aligning tool and the cellular sampling tool is impeded when the retaining cover is engaged, and distal movement is permitted when the retaining cover is removed.

3. The device of claim 1, wherein distal movement of the cellular sampling tool is released by a retaining mechanism comprising a manual release tab on the sampling tool in disengaging communication with the insertion tube, wherein distal movement of the cellular sampling tool is impeded when the pin is engaged when the sampling tool is in the first position, and distal movement is permitted when the tab is manually disengaged.

4. The device of claim 1, wherein distal movement of the cellular sampling tool is released by a retaining mechanism comprising a biased release pin on the sampling tool in selective communication with the insertion tube, wherein distal movement of the cellular sampling tool is impeded by the pin in communication with the insertion tube when the alignment tool and sampling tool are in the first position, and distal movement of the cellular sampling tool is permitted when the alignment tool is in the second position automatically releasing the biased pin from communication with the insertion tube.

5. The device of claim 1, wherein the cellular sampling tool is rotatable within the insertion tube and upon the cervical aligning tool handle.

6. The device of claim 1, wherein the distal end of cellular adhesion surface is an abrasive brush element with a looped wire with bristle configuration.

7. The device of claim 1, wherein the cellular adhesion surface is separable from the cellular sampling tool.

8. The device of claim 1, where the cellular sampling tool further comprises a retaining element disposed upon the sampling tool between a first position for retaining the adhesion surface and a second position for releasing the adhesion surface.

9. The device of claim 1, wherein the cervical aligning probe is spoon-shaped having a convex curvature concentric with the distal end of the insertion tube.

10. The device of claim 1, wherein the cervical aligning tool further comprises an aligning extension element extending along a portion of the body which engages an elongated alignment groove extending from the interior surface of the insertion tube.

11. The device of claim 1, wherein the handle of the cervical aligning tool engages the proximal portion of the passage of the insertion tube to impede further distal movement of the cervical aligning tool within the vagina.

12. The device of claim 1, wherein the advancing handle of the cellular sampling tool engages the proximal portion of the handle of the cervical aligning tool to impede further distal movement of cellular sampling tool within the vagina.

13. The device of claim 1, wherein the proximal end of the insertion tube further comprises an annular insertion shield peripherally extending from the exterior surface to impede insertion within the vagina beyond a predetermined depth.

14. The device of claim 13, wherein the annular insertion shield extends wider along a surface corresponding to the anterior of the vaginal opening and narrower along an opposite surface corresponding to the posterior of the vaginal opening to guide the patient as to the proper orientation for insertion.

15. The device of claim 1, wherein the proximal end of the insertion tube further comprises a plurality of exterior ribbed gripping surfaces proximal to the insertion shield.

16. The device of claim 1, wherein the proximal end of the insertion tube has a diameter greater than the distal end of the insertion tube.

17. A method of collecting a cervical tissue sample from a patient comprising:
  (a) inserting into the vagina of the patient a device comprising:
    (i) an elongated insertion tube shaped for insertion into the vagina and having a proximal end, a distal end, an exterior surface and a passage extending therethrough defining an interior surface;
    (ii) an elongated cervical aligning tool shaped for insertion within the passage of the insertion tube and having a proximal end with an advancing handle thereon, a distal end with a cervical aligning probe thereon and a body therebetween, wherein the advancing handle extends from the proximal passage of the insertion tube and is movable between a first position for insertion wherein the distal cervical aligning probe is contained within the passage of the insertion tube, and a second position for cervical cap alignment wherein the distal cervical aligning probe extends distally from the passage of the insertion tube; and
    (iii) an elongated cellular sampling tool shaped for insertion within the passage of the insertion tube, and having a proximal end with an advancing handle thereon, a distal end with a cellular adhesion surface thereon, wherein the advancing handle extends from the proximal passage of the insertion tube, and is movable between a first position for insertion wherein the distal cellular adhesion surface is contained within the passage of the insertion tube, and a second position for cervical cell tissue sampling wherein the distal cellular adhesion surface extends distally from the passage of the insertion tube;
  (b) advancing the handle of the cervical aligning tool distally from within the insertion tube in the first position to the second position for cervical cap alignment to engage the cervical fornix of the patient;
  (c) moving the elongated cellular sampling tool distally from the first position to the second position for cervical cell tissue sampling;
  (d) rotating the cellular sampling tool to capture cervical tissue at the patient's os on the cellular adhesion surface;
  (e) moving the elongated cellular sampling tool proximally from the second position to the first position to shield the cervical tissue sample within the insertion tube; and
  (f) withdrawing the device from the vagina of the patient.

18. The method of claim 17, wherein the device further comprises a handle retaining mechanism comprising a handle retaining cover having a proximal end, a distal end, comprising an insertion tube engaging surface, and a cellular sampling tool engaging surface, wherein the handle retaining cover is releasably engaged with the device such that movement of the cellular sampling tool is impeded when engaged and permissible when released.

19. The method of claim 17, further comprising the later steps of separating the cellular adhesion surface from the cellular sampling tool; and placing the cellular adhesion surface in a container of cellular preservative.

20. A kit for cervical cell tissue sampling comprising the device of claim 1, one or more replacement cellular adhesion surfaces; one or more containers of cellular preservative, and instructions for use of the device to obtain a cervical cellular tissue sample and preserve the sample in the container.

* * * * *

UNITED STATES PATENT AND TRADEMARK OFFICE
CERTIFICATE OF CORRECTION

Page 1 of 1

PATENT NO.         : 9,282,950 B2
APPLICATION NO.    : 14/192989
DATED              : March 15, 2016
INVENTOR(S)        : Philip Klein It is certified that error appears in the above-identified patent and that said Letters Patent is hereby corrected as shown below:

In the Claims

At column 16, line 1, delete "end with a" before "handle".

At column 16, line 4, delete "proximal passage of the" before "insertion".

At column 16, line 13, delete "end with an" before "advancing".

At column 16, line 15, delete "proximal passage of the" after "from the".

At column 16, line 23, delete "released" and insert --regulated--.

At column 16, line 34, delete "released" and insert --regulated--.

At column 16, line 42, delete "released" and insert --regulated--.

At column 17, line 40, delete "end with an" before "advancing".

At column 17, line 43, delete "proximal passage of the" before "insertion".

Signed and Sealed this
Seventeenth Day of May, 2016

Michelle K. Lee
*Director of the United States Patent and Trademark Office*